(12) United States Patent
Hwang et al.

(10) Patent No.: US 8,545,220 B2
(45) Date of Patent: Oct. 1, 2013

(54) ORTHODONTIC TREATMENT TUBE

(75) Inventors: Hyeon Shik Hwang, Gwangju-si (KR);
Woo Seok Shin, Gyeonggi-do (KR)

(73) Assignee: Hubit Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/280,605

(22) Filed: Oct. 25, 2011

(65) Prior Publication Data

US 2012/0129121 A1    May 24, 2012

(30) Foreign Application Priority Data

Nov. 18, 2010   (KR) .................. 10-2010-0115068

(51) Int. Cl.
*A61C 3/00*    (2006.01)

(52) U.S. Cl.
USPC ............................................. 433/17

(58) Field of Classification Search
USPC .............................. 433/8–18, 22, 24
See application file for complete search history.

(56) References Cited

U.S. PATENT DOCUMENTS

| | | | | | |
|---|---|---|---|---|---|
| 3,055,110 | A | * | 9/1962 | Kesling | 433/10 |
| 3,494,034 | A | * | 2/1970 | Kesling | 433/17 |
| 4,533,320 | A | * | 8/1985 | Piekarsky | 433/9 |
| 4,948,367 | A | * | 8/1990 | Haas | 433/9 |
| 5,306,142 | A | * | 4/1994 | Richards | 433/22 |
| 5,320,526 | A | * | 6/1994 | Tuneberg | 433/17 |
| 5,464,349 | A | * | 11/1995 | Andreiko et al. | 433/24 |
| 5,556,277 | A | * | 9/1996 | Yawata et al. | 433/17 |
| 5,707,232 | A | * | 1/1998 | Strauss et al. | 433/17 |
| 5,927,971 | A | * | 7/1999 | De Baets | 433/17 |
| 6,039,564 | A | * | 3/2000 | Hendrick | 433/17 |
| 6,206,690 | B1 | * | 3/2001 | Vargas | 433/9 |
| 6,217,322 | B1 | * | 4/2001 | Kesling | 433/17 |
| 6,554,613 | B1 | * | 4/2003 | Sachdeva et al. | 433/24 |
| 6,709,268 | B2 | * | 3/2004 | Pospisil et al. | 433/17 |
| 6,749,426 | B2 | * | 6/2004 | Devanathan | 433/9 |
| 7,160,106 | B2 | * | 1/2007 | Farzin-Nia et al. | 433/22 |
| 7,214,056 | B2 | * | 5/2007 | Stockstill | 433/3 |
| 7,780,442 | B2 | * | 8/2010 | Kesling | 433/9 |
| 2003/0064343 | A1 | * | 4/2003 | Devanathan | 433/9 |
| 2003/0134250 | A1 | * | 7/2003 | McGann | 433/4 |
| 2010/0151405 | A1 | * | 6/2010 | Marshall | 433/24 |
| 2011/0053108 | A1 | * | 3/2011 | Ariza | 433/17 |
| 2011/0151392 | A1 | * | 6/2011 | Ariza | 433/17 |
| 2011/0311933 | A1 | * | 12/2011 | Parker | 433/9 |

FOREIGN PATENT DOCUMENTS

JP         04309346 A    * 10/1992

* cited by examiner

*Primary Examiner* — Cris L Rodriguez
*Assistant Examiner* — Matthew Saunders
(74) *Attorney, Agent, or Firm* — Rabin & Berdo, P.C.

(57) ABSTRACT

Provided is an orthodontic treatment including a main tube, and a pair of caps provided at both ends of the main tube to form an adhesion space therebetween in which an adhesive is accommodated and the adhesive is prevented from flowing into the main tube through an insertion hole of the main tube. Since the adhesive is applied to the adhesion space formed by fitting the pair of caps onto the outer circumference of the main tube, the caps can prevent the applied adhesive flowing into the main tube and the wire can be easily inserted into the main tube.

4 Claims, 6 Drawing Sheets

(S1)

(S2)

(S3)

ORTHODONTIC TREATMENT TUBE

CROSS-REFERENCE TO RELATED APPLICATION

This application claims priority to and the benefit of Korean Patent Application No. 2010-0115068, filed on Nov. 18, 2010, the disclosure of which is incorporated herein by reference in its entirety.

BACKGROUND

1. Field of the Invention

The present invention relates to an orthodontic instrument, and more particularly, to an orthodontic treatment tube.

2. Description of the Related Art

In general, in dental terminology, a state in which a tooth is crooked or a set of teeth is uneven is referred to as "malocclusion," and treatment for correcting the malocclusion is referred to as orthodontic treatment.

When teeth are in malocclusion, the face becomes distorted, chewing food becomes difficult, and air is leaked between teeth which can impede speech, causing various handicaps.

Accordingly, various orthodontic appliances are developed and used to correct the teeth, thus overcoming these handicaps. In general, a conventional orthodontic appliance includes a bracket having a pair of fixing wings disposed at both sides thereof, a correcting wire, and a fastening tie.

The orthodontic appliance using the bracket is mounted and used for several months to several years.

However, among orthodontic patients, when the orthodontic appliance having the bracket cannot be easily applied or partial orthodontic treatment is needed, orthodontic therapy using a small hollow tube is used.

Referring to FIGS. 1A, 1B and 1C, the orthodontic therapy using a conventional tube is performed in a sequence of tube cutting S1, tube bonding S2, and wire insertion S3.

In the tube cutting S1, a small hollow tube 1 having an inner diameter of 0.4 to 0.6 mm is cut into a predetermined length to manufacture a tube 2 used for tooth correction.

In the tube bonding S2, the tubes 2 are adhered to teeth 3 to be orthodontically treated using an adhesive 4.

In the wire insertion S3, after inserting a wire 5 into the tubes 2 adhered to the teeth 3, both ends of the inserted wire 5 are bent to perform orthodontic treatment using the tubes 2.

However, the orthodontic therapy using the conventional tube 2 has the following problems.

First, when the tube 2 is adhered to the tooth 3, as the adhesive 4 flows into the tube 2 through both side holes of the tube 2 and hardens, it is difficult or impossible to insert the wire 5 into the tube 2. In particular, in order to avoid this problem, when a small amount of adhesive 4 is applied to the tube 2, the tube 2 may be easily separated from the tooth 3 due to reduction in adhesive strength.

Second, the adhesive 4 is applied at a center of an outer circumference of the tube 2 in a convex shape, rather than evenly applied to the entire outer circumference, degrading the appearance.

Third, in the case of the tooth 3 having an uneven surface, the tube 2 must be adhered to the tooth surface while adjusting a height of the tube 2 with respect to the tooth surface. However, since the height of the tube 2 cannot be separately adjusted, an operator has to adjust an attachment height of the tube by adjusting an amount of the adhesive 4. In practice, it is difficult for the operator to adjust the amount of the adhesive 4 and thus the attachment height of the tube 3 to a desired level.

Fourth, when the tube 2 is separated from the tooth 3, the operator picks up the center of the tube 2 and grips both sides of the tube 2 with an appropriate force using a tool such as pliers, and shakes the tube 2 adhered to the tooth 2 to separate the tube 2 from the tooth 3. However, since the conventional tube 2 is small, it is difficult to grip both sides of the tube 2 to apply the appropriate force.

Fifth, since the conventional tube 2 is small, when an adhesion direction of the tube 2 deviates while the tube 2 is being attached to the tooth surface to perform orthodontic treatment, it is difficult for the operator to check deviation in the adhesion direction of the tube 2. As a result, deviation of the entire arrangement of the tubes 2 for orthodontic treatment causes a troublesome correction operation.

Sixth, when a dental cast tray is used to attach the conventional tube 2 to the tooth surface through an indirect attachment method, in order to increase adhesion strength of the tube 2 disposed on the dental cast tray, sandblasting is performed on a surface of the tube 2. At this time, the tube 2 may be easily separated from the dental cast tray.

SUMMARY OF THE INVENTION

In order to solve these problems, an aspect of the present invention is to provide an orthodontic treatment tube including a main tube, and a pair of caps installed at both sides of the main tube to receive an adhesive therebetween and form an adhesion space for preventing the adhesive from flowing into the main tube through an insertion hole of the main tube.

Another aspect of the present invention is to provide an orthodontic treatment tube in which an attachment height of the main tube attached to a tooth surface can be adjusted by partially removing one or both of the pair of caps installed at both ends of the main tube to a desired height.

Still another aspect of the present invention is to provide an orthodontic treatment tube in which the adhesion space formed at an outer circumference of the main tube by the pair of caps can form an orthodontic hole in a vertical direction of the main tube to fasten a wire configured to correct a direction of the tooth that deviates between the tooth surface and the adhesion space when an operator applies the adhesive to the adhesion space.

Yet another aspect of the present invention is to provide an orthodontic treatment tube further including a tube guide inserted into the main tube to project from both sides of the main tube by a predetermined length so that the operator can easily check the deviation state of the adhesion direction of the main tube during adhesion of the main tube to the tooth surface for orthodontic treatment.

Yet another aspect of the present invention is to provide an orthodontic treatment tube including a main-tube insertion tube, into which the main tube is inserted, having a pair of flanges projecting from both ends of an outer circumference thereof to a predetermined width such that the adhesion space is formed therebetween to accommodate the adhesive and prevent the adhesive from flowing into the main tube through the insertion hole of the main tube.

Yet another aspect of the present invention is to provide an orthodontic treatment tube in which an attachment height of the main-tube insertion tube attached to the tooth surface can be adjusted by partially removing one or both of the pair of flanges installed at both ends of the main-tube insertion tube to a desired height.

Yet another aspect of the present invention is to provide an orthodontic treatment tube in which the adhesion space formed at an outer circumference of the main-tube insertion tube by the pair of flanges can form an orthodontic hole in a vertical direction of the main-tube insertion tube to fasten a wire configured to correct a direction of the tooth that deviates between the tooth surface and the adhesion space when the operator applies the adhesive to the adhesion space.

Yet another aspect of the present invention is to provide an orthodontic treatment tube further including a tube guide inserted into the main tube to project from both sides of the main-tube insertion tube by a predetermined length so that the operator can easily check the deviation state of the adhesion direction of the main-tube insertion tube during adhesion of the main-tube insertion tube to the tooth surface for orthodontic treatment.

In order to accomplish the above aspects, there is provided an orthodontic treatment tube including: a main tube through which an insertion hole is formed; and a pair of caps fitted onto both ends of an outer circumference of the main tube to a predetermined width to form an adhesion space therebetween in which an adhesive is accommodated and the adhesive is prevented from flowing into the main tube through the insertion hole of the main tube.

Here, one or both of the pair of caps may be partially removed to adjust an attachment height of the main tube attached to a tooth surface.

In addition, an orthodontic hole into which a wire can be fastened between the tooth surface and the adhesion space to correct a direction of the tooth may be formed in a direction perpendicular to the main tube when the adhesive is applied to the adhesion space formed on the outer circumference of the main tube by the pair of caps.

Further, the orthodontic treatment tube may further include a tube guide inserted into the insertion hole of the main tube and having both ends projecting from both sides of the main tube by a predetermined length so that an adhesion direction deviation state of the main tube can be easily checked during adhesion of the main tube to the tooth surface for orthodontic treatment.

There is also provided an orthodontic treatment tube including: a main tube through which an insertion hole is formed; and a main-tube insertion tube having an insertion hole into which the main tube is inserted, and a pair of flanges projecting from both ends of an outer circumference thereof to a predetermined width to form an adhesion space therebetween in which an adhesive is accommodated and the adhesive is prevented from flowing into the main tube through the insertion hole of the main tube.

Here, one or both of the pair of flanges may be partially removed to adjust an attachment height of the main-tube insertion tube attached to a tooth surface.

In addition, an orthodontic hole into which a wire can be fastened between the tooth surface and the adhesion space to correct a direction of the tooth may be formed in a direction perpendicular to the main-tube insertion tube when the adhesive is applied to the adhesion space formed on the outer circumference of the main-tube insertion tube by the pair of flanges.

Further, the orthodontic treatment tube may further include a tube guide inserted into the insertion hole of the main tube inserted into the main-tube insertion tube and having both ends projecting from both sides of the main-tube insertion tube by a predetermined length so that an adhesion direction deviation state of the main-tube insertion tube can be easily checked during adhesion of the main-tube insertion tube to the tooth surface for orthodontic treatment.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Embodiment 1

Figure 1A:
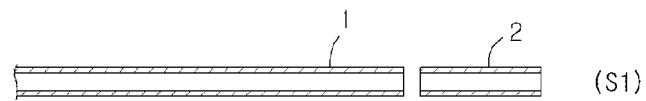
FIG. 1A is a view for explaining a first step of an embodiment of orthodontic therapy using a conventional tube.
Figure 1B:
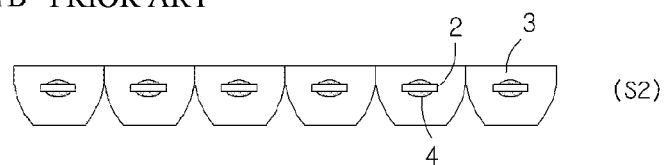
FIG. 1B is a view for explaining a second step of an embodiment of orthodontic therapy using a conventional tube.
Figure 1C:
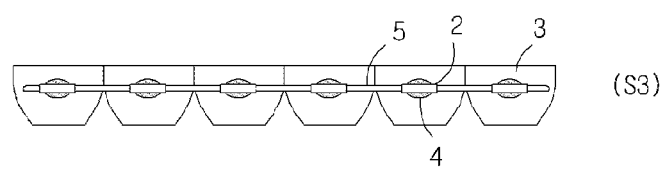
FIG. 1C is a view for explaining a third step of an embodiment of orthodontic therapy using a conventional tube.
Figure 2:
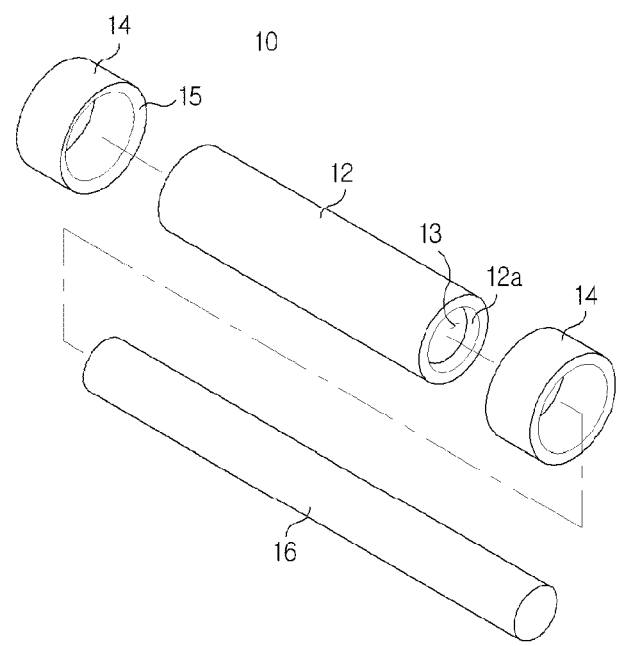
FIG. 2 is an exploded perspective view of a tube in accordance with a first exemplary embodiment of the present invention.
Figure 3:
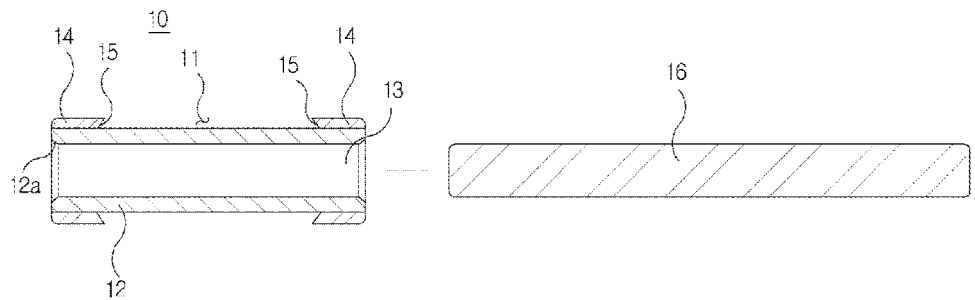
FIG. 3 is a cross-sectional view of the tube in accordance with the first exemplary embodiment of the present invention.

Referring to FIGS. 2 and 3, a tube 10 in accordance with a first exemplary embodiment of the present invention includes a main tube 12, and a pair of caps 14 installed at both ends of the main tube 12. According to necessity, the tube 10 may further include a tube guide 16 inserted into the main tube 12 and having both ends projecting from both sides of the main tube 12 by a predetermined length.

The main tube 12 has a hollow tube shape with an insertion hole 13 passing through a center thereof, and according to necessity, the tube guide 16 is inserted into the insertion hole 13.

Main-tube enlarged parts 12a may be formed at both ends of the insertion hole 13 of the main tube 12 through inside chamfering or inside rounding such that the tube guide 16 and a correction wire can be easily inserted.

The main tube 12 may be formed of a metal material.

The pair of caps 14 are fitted onto both ends of the outer circumference of the main tube 12 to a predetermined width to form an adhesion space 11 configured to accommodate an adhesive therebetween and prevent the adhesive from flowing into the main tube 12 through the insertion hole 13 of the main tube 12.

The caps 14 are formed of a resin for dental treatment or a polymer resin through, preferably, injection molding or bonding.

A cap enlarged part 15 formed through inside chamfering is formed at one end of the cap 14. The cap enlarged part 15 can drive the adhesive applied to the adhesion space 11 between the main tube 12 and the cap 14 to penetrate the cap enlarged part 15 and be solidified, increasing a fixing force between the tube 10 in accordance with the first exemplary embodiment of the present invention and the tooth surface.

One or both of the pair of caps 14 may be partially removed to adjust an attachment height of the main tube 12 attached to the tooth surface.

The tube guide 16 is inserted into the insertion hole 13 of the main tube 12 such that an operator can easily check an adhesion direction deviation state of the main tube during adhesion of the main tube 12 to the tooth surface for orthodontic treatment, and projects from both sides of the main tube 12 by a predetermined length.

The tube guide 16 may have a diameter equal to or smaller than that of the insertion hole 13 of the main tube 12.

The above-mentioned orthodontic treatment tube 10 in accordance with the first exemplary embodiment of the present invention is used as described below.

Figure 4A:
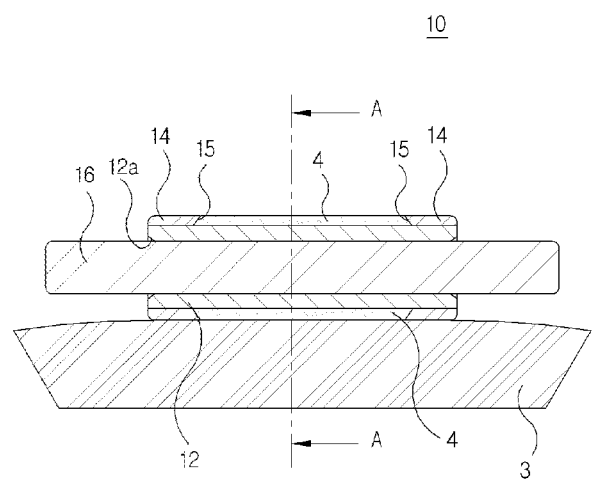
FIG. 4A is a cross-sectional view showing a state in which the tube in accordance with the first exemplary embodiment of the present invention is attached to a tooth.
Figure 4B:
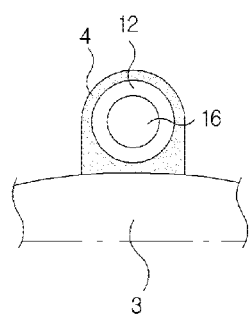
FIG. 4B is a cross-sectional view along the line AA in FIG. 4A.

Referring to FIGS. 4A and 4B, the operator directly attaches the tube 10 constituted by the main tube 12 with the caps installed at both ends thereof to the tooth 3 to be corrected, or attaches the tube 10 to a dental cast tray of a patient.

Alternatively, when the operator inserts the tube guide 16 into the insertion hole 13 of the main tube 12 to attach the tube 10 to the tooth 3, the operator can check the tube guide 16 projecting from both sides of the main tube 12 by a predetermined length with the naked eye, easily checking the adhesion direction deviation state of the main tube 12. When the tube 10 is adhered to the tooth 3 using the tube guide 16 for orthodontic treatment, after completion of the adhesion of the tube 10, the tube guide 16 is removed from the main tube 12.

For reference, when the operator uses a dental cast tray to attach the tube 10 to the tooth surface through an indirect attachment procedure, since the main tube 12 having the pair of caps 14 installed at both ends thereof or the main tube 12 having the pair of caps 14 installed at both of the ends and the insertion hole 13 into which the tube guide 16 is inserted is disposed on the dental cast tray, even when the main tube 12 is surface-treated through sandblasting to increase adhesion strength of the main tube 12 disposed on the dental cast tray, the tube 10 cannot be easily separated from the dental cast tray in comparison with the case in which only the conventional tube 2 is disposed on the dental cast tray.

When the tube 10 is adhered to the tooth 3 for orthodontic treatment as described above, while the adhesive 4 is applied to the adhesion space 11 formed at the outer circumference of the main tube 12 by the pair of caps 14 and the applied adhesive 4 spreads evenly according to the outer circumference of the main tube 12 to be solidified, it is possible to prevent the adhesive 4 from flowing into the main tube 12 due to a height corresponding to a thickness of the pair of caps 14 installed at both ends of the main tube 12.

As described above, when the adhesive is evenly applied to the entire adhesion space 11, the main tube 12 can be securely adhered to the tooth 3 with sufficient adhesion strength and good appearance. In particular, after the tube 10 is completely adhered to the tooth 3, a wire 5 can be easily inserted into the main tube 12.

In addition, when the operator attaches the tube 10 to the tooth 3 having an uneven tooth surface, according to necessity, the attachment height of the main tube 12 can be easily adjusted by partially removing one or both of the pair of caps 14.

Further, when the tube 10 is to be removed after complete adhesion of the tube 10 to the tooth 3 for orthodontic treatment or the tube 10 is to be removed after completion of the orthodontic treatment, since the operator can pick up a center of the main tube 12 to easily grip the pair of caps 14 installed at both sides of the main tube 12 with a tool such as pliers, the tube 10 can be relatively easily separated from the tooth 3 in comparison with the conventional tube 2.

Figure 5A:
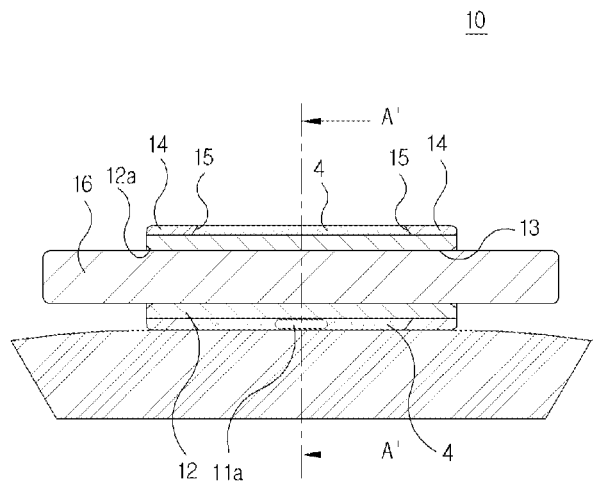
FIG. 5A is a cross-sectional view showing a state in which an orthodontic hole is formed in FIG. 4A.
Figure 5B:
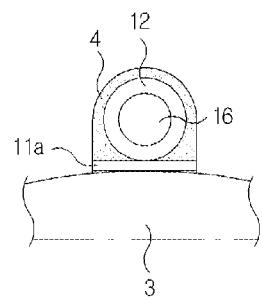
FIG. 5B is a cross-sectional view along the line A'A' in FIG. 5A.

Meanwhile, referring to FIGS. 5A and 5B, during adhesion of the tube 10 to the tooth 3 for orthodontic treatment, when a deviated tooth such as an inturned tooth of the teeth 3 is to be corrected, the operator can form an orthodontic hole 11a, through which the wire 5 configured to correct a direction of the deviated tooth 3 can be fastened between the tooth surface and the adhesion space 11 when the adhesive 4 is applied to the adhesion space 11, in a direction perpendicular to the main tube 12. For example, the orthodontic hole 11a may be formed by not applying the adhesive 4 to a portion at which the orthodontic hole 11a is to be formed when the adhesive 4 is applied to the adhesion space 11, or by removing the wire 5 at an appropriate time after positioning the wire 5 to the portion at which the orthodontic hole 11a is to be formed to apply the adhesive 4 and before the applied adhesive 4 is solidified.

Figure 6:
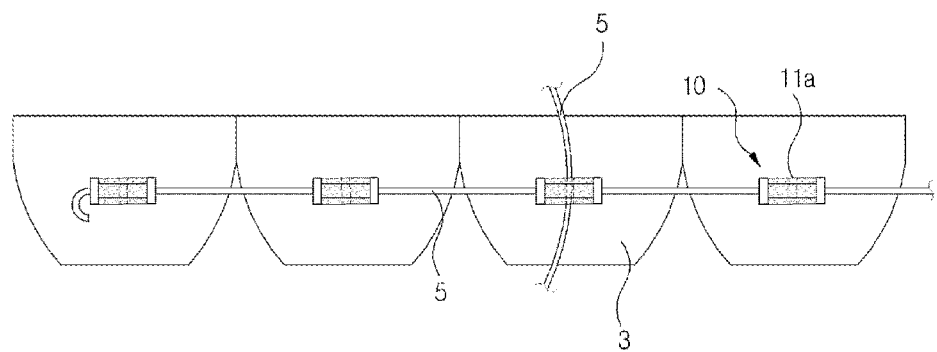
FIG. 6 is a view showing a state in which a wire is fastened to the orthodontic hole of FIG. 5A to correct a direction of a deviated tooth.

When the orthodontic hole 11a is formed as described above, after completely attaching the tube 10 to the tooth 3 for orthodontic treatment, as shown in FIG. 6, the operator inserts the wire 5 into the tubes 10 adhered to the teeth 3 and then bends both ends of the inserted wire 5, performing the orthodontic treatment using the tube 10.

Here, when the direction of the deviated tooth 3 such as an inturned tooth is to be corrected, the operator inserts the wire 5 into the orthodontic hole 11a formed in a direction perpendicular to the main tube 12 and then inserts the wire 5 into the orthodontic hole 11a of another adjacent tooth 3 to tighten the wire 5 such that a force of correcting the direction of the deviated tooth 3 can be received or to fix both ends thereof using a separate tightening mechanism or fastening mechanism, correcting the direction of the deviated tooth 3.

Second Embodiment

Figure 7:
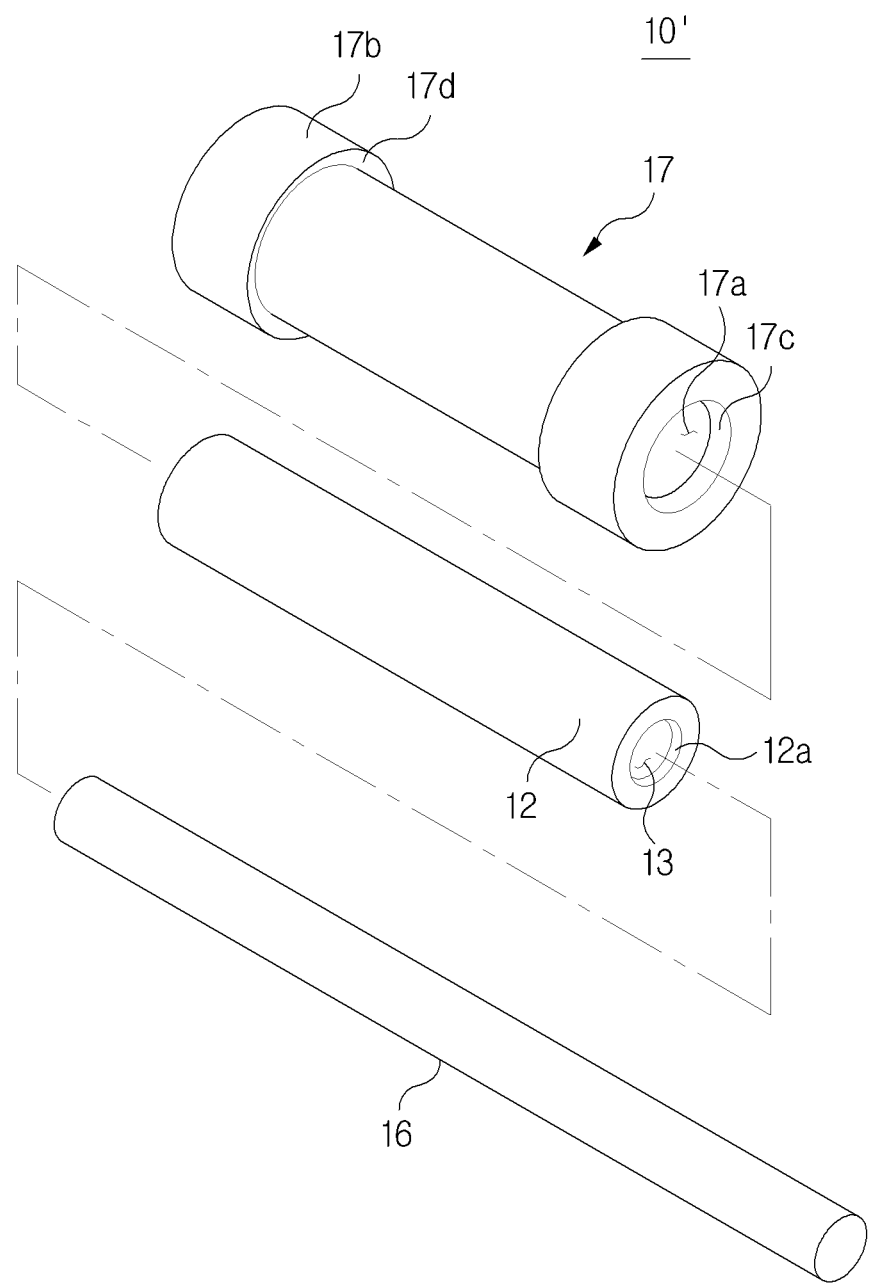
FIG. 7 is an exploded perspective view of a tube in accordance with a second exemplary embodiment of the present invention.
Figure 8:
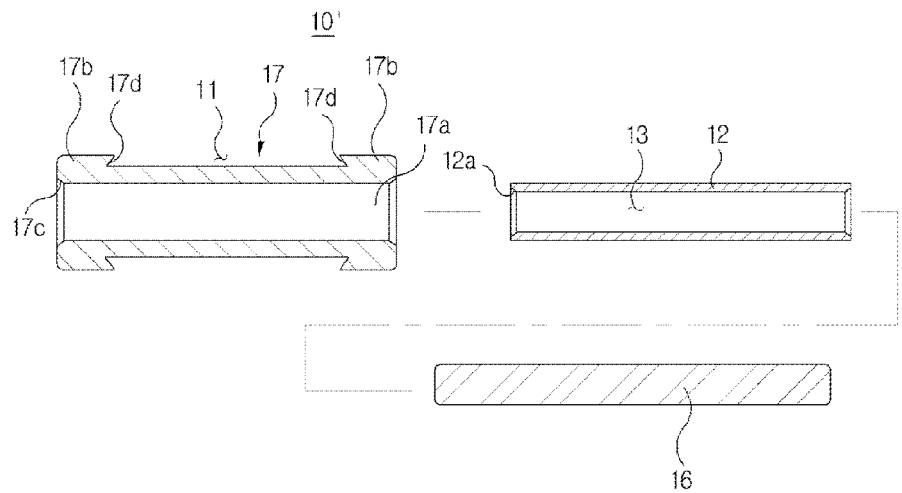
FIG. 8 is a cross-sectional view of the tube in accordance with the second exemplary embodiment of the present invention.

FIGS. 7 and 8 are an exploded perspective view and a cross-sectional view of the tube 10' in accordance with a second exemplary embodiment of the present invention, respectively.

As described in the tube 10 in accordance with the first exemplary embodiment of the present invention, when the adhesive 4 is applied to the adhesion space 11 formed on the outer circumference of the main tube 12 by the pair of caps 14, a color of the main tube 12 formed of a metal and exposed through the applied adhesive, which is transparent or semi-transparent, is contrastive to a color of the tooth 3, which degrades the appearance after the main tube 12 is adhered to the tooth 3 for orthodontic treatment, causing psychological repulsion of the orthodontic patient.

Accordingly, in order to solve the problems of the tube 10 in accordance with the first exemplary embodiment of the present invention, the second embodiment of the present invention exemplarily provides the improved tube 10', in which a main-tube insertion tube 17 having an insertion hole 17*a* through which the main tube 12 is press-fitted is adhered to the tooth 3.

According to the second embodiment of the present invention, since the main tube 12 formed of a metal is inserted into the main-tube insertion tube 17 to be covered therewith, the second embodiment has a better appearance than the first embodiment of the present invention to which the main tube 12 is directly attached to the tooth 3.

In FIGS. 7 and 8, and FIGS. 9 to 11 referenced in the following description, like reference numerals of the components of the tube 10 in accordance with the first exemplary embodiment of the present invention designate like components of the tube 10' in accordance with the second exemplary embodiment of the present invention.

In addition, hereinafter, overlapping description of the tube 10 in accordance with the first exemplary embodiment of the present invention will not be repeated, and configurations and operations related to the main-tube insertion tube 17 of the tube 10' in accordance with the second exemplary embodiment of the present invention will be mainly described.

As shown in FIGS. 7 and 8, the tube 10' in accordance with the second exemplary embodiment of the present invention includes the main tube 12 and the main-tube insertion tube 17, and according to necessity, may further include a tube guide 16 inserted into the main tube 12 and having both ends projecting from both sides of the main-tube insertion tube 17 by a predetermined length.

The main tube 12 is press-fitted into the main-tube insertion tube 17 to be fixed thereto.

The main-tube insertion tube 17 has an insertion hole 17*a* through which the main tube 12 is inserted, and a pair of flanges 17*b* projecting from both ends of an outer circumference thereof to a predetermined width to form an adhesion space 11 therebetween, in which the adhesive 4 is accommodated and prevented from flowing into the main tube 12 through the insertion hole 13 of the main tube 12.

Insertion tube enlarged parts 17*c* may be formed at both ends of the insertion hole 17*a* of the main-tube insertion tube 17 through inside chamfering or inside rounding such that the main tube 12 can be easily inserted.

The main-tube insertion tube 17 is formed of a resin for dental treatment or a polymer resin through, preferably, injection molding or bonding.

The pair of flanges 17*b* of the main-tube insertion tube 17 have adhesive penetration grooves 17*d* formed at one ends facing each other and inclined toward ends of the main-tube insertion tube 17 through undercut machining. The adhesive penetration grooves 17*d* are configured such that the adhesive applied to the adhesion space 11 between the main-tube insertion tube 17 and the flanges 17*b* penetrates the adhesive penetration grooves 17*d* to be solidified, increasing a fixing force between the tube 10' in accordance with the second exemplary embodiment of the present invention and the tooth surface.

One or both of the pair of flanges 17*b* may be partially removed to be used in order to adjust an attachment height of the main-tube insertion tube 17 attached to the tooth surface.

The tube guide 16 is inserted into the insertion hole 13 of the main tube 12 inserted into the main-tube insertion tube 17 to project both ends thereof from both sides of the main-tube insertion tube 17 by a predetermined length such that the operator can easily check an adhesion direction deviation state of the main-tube insertion tube 17 during adhesion of the main-tube insertion tube 17 to the tooth surface for orthodontic treatment.

The tube guide 16 may have a diameter equal to or slightly smaller than that of the insertion hole 13 of the main tube 12.

The orthodontic treatment tube 10' in accordance with the second exemplary embodiment of the present invention is used as described below.

Figure 9A:
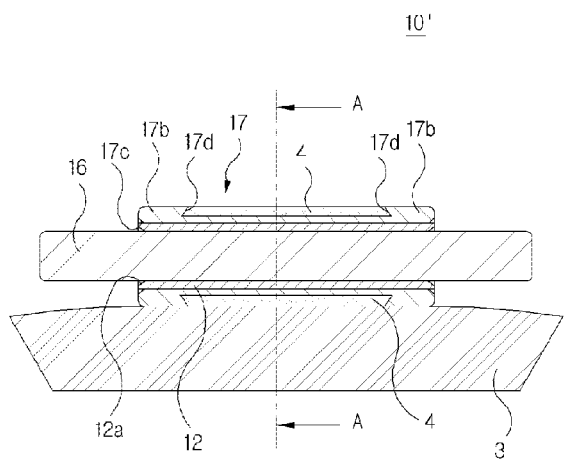
FIG. 9A is a cross-sectional view showing a state in which another tube in accordance with the second exemplary embodiment of the present invention is attached to a tooth.
Figure 9B:
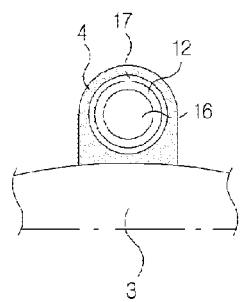
FIG. 9B is a cross-sectional view along the line AA in FIG. 9A.

Referring to FIGS. 9A and 9B, the operator directly attaches the tube 10' constituted by the main-tube insertion tube 17 having the flanges 17*b* formed at both ends and the insertion hole 17*a*, into which the main tube 12 is inserted, to the tooth 3 to be corrected, or attaches the tube 10' to a dental cast tray for a patient to be treated.

Alternatively, when the operator inserts the tube guide 16 into the insertion hole 13 of the main tube 12 and attaches the tube 10' to the tooth 3, the operator can easily check an adhesion direction deviation state of the main-tube insertion tube 17 while checking the tube guide 16 projecting from both sides by a predetermined length with the naked eye. When the tube 10' is adhered to the tooth 3 using the tube guide 16 for orthodontic treatment, after completion of the adhesion of the tube 10', the tube guide 16 is extracted from the main tube 12 inserted into the main-tube insertion tube 17.

For reference, when the operator uses the dental cast tray to attach the tube 10' to the tooth surface through an indirect attachment method, the pair of flanges 17*b* are formed at both ends of the dental cast tray and the main-tube insertion tube 17 into which the main tube 12 is press-fitted is disposed therein, or the pair of flanges 17*b* are formed at both ends thereof and the main-tube insertion tube 17 into which the tube guide 16 is inserted is disposed in the main tube 12 press-fitted thereinto. Accordingly, even when the main-tube insertion tube 17 is surface-treated through sandblasting in order to increase the adhesion strength of the main-tube insertion tube 17 disposed on the dental cast tray, the tube 10' cannot be easily separated from the dental cast tray in comparison with the case in which only the conventional tube 2 is disposed on the dental cast tray.

When the tube 10' is adhered to the tooth 3 for orthodontic treatment, the adhesive 4 is applied to the adhesion space 11 formed on the outer circumference of the main-tube insertion tube 17 by the pair of flanges 17*b*. While the applied adhesive 4 is evenly spread along the outer circumference of the main-tube insertion tube 17 to be solidified, the adhesive 4 is prevented from flowing into the main tube 12 inserted into the insertion hole 17*a* of the main-tube insertion tube 17 due to a height corresponding to a thickness of the pair of flanges 17*b* formed at both ends of the main-tube insertion tube 17.

When the adhesive 4 is evenly applied to the entire adhesion space 11 as described above, the main-tube insertion tube 17 can be securely fixed to the tooth 3 with sufficient adhesion strength and good appearance. In particular, after completely attaching the tube 10' to the tooth 3, the wire 5 can be inserted into the main tube 12.

In addition, when the operator attaches the tube 10' to the tooth 3 having an uneven tooth surface, according to necessity, the attachment height of the main-tube insertion tube 17 can be easily adjusted by partially removing one or both of the pair of flanges 17b.

Further, after completely attaching the tube 10' to the tooth 3 for orthodontic treatment, when the tube 10' is to be removed or the tube 10' is to be removed from the tooth 3 after completion of the orthodontic treatment, since the operator can easily pick up a center of the main-tube insertion tube 17 to grip the pair of flanges 17b formed at both sides of the main-tube insertion tube 17 with a tool such as pliers, the tube 10' can be relatively easily separated from the tooth 3 in comparison with the conventional tube 2.

Figure 10A:
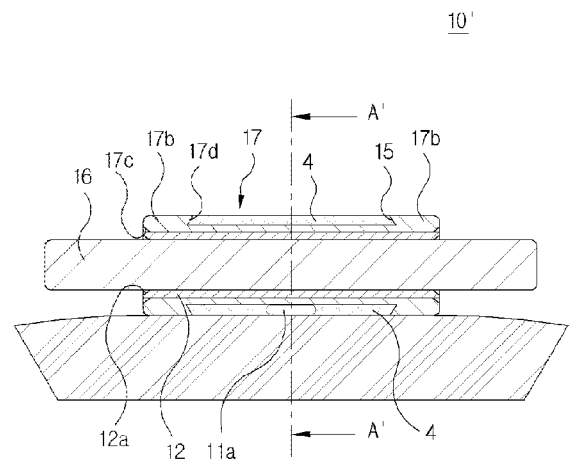
FIG. 10A is a cross-sectional view showing a state in which an orthodontic hole is formed in FIG. 9A.
Figure 10B:
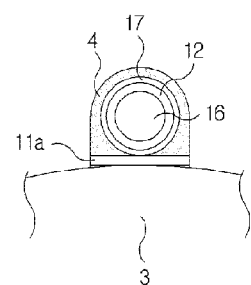
FIG. 10B is a cross-sectional view along the line A'A' in FIG. 10A.

Meanwhile, referring to FIGS. 10A and 10B, during adhesion of the tube 10' to the tooth 3 for orthodontic treatment, when a direction of the deviated tooth 3 such as an inturned tooth 3 of the teeth 3 is to be corrected, the operator can form an orthodontic hole 11a in a direction perpendicular to the main-tube insertion tube 17 such that the wire 5 can be fastened between the tooth surface and the adhesion space 11 to correct the direction of the deviated tooth 3 when the adhesive 4 is applied to the adhesion space 11. For example, the orthodontic hole 11a may be formed by not applying the adhesive 4 to a portion at which the orthodontic hole 11a is to be formed when the adhesive 4 is applied to the adhesion space 11, or by removing the wire 5 at an appropriate time after positioning the wire 5 to the portion at which the orthodontic hole 11a is to be formed to apply the adhesive 4 and before the applied adhesive 4 is solidified.

Figure 11:
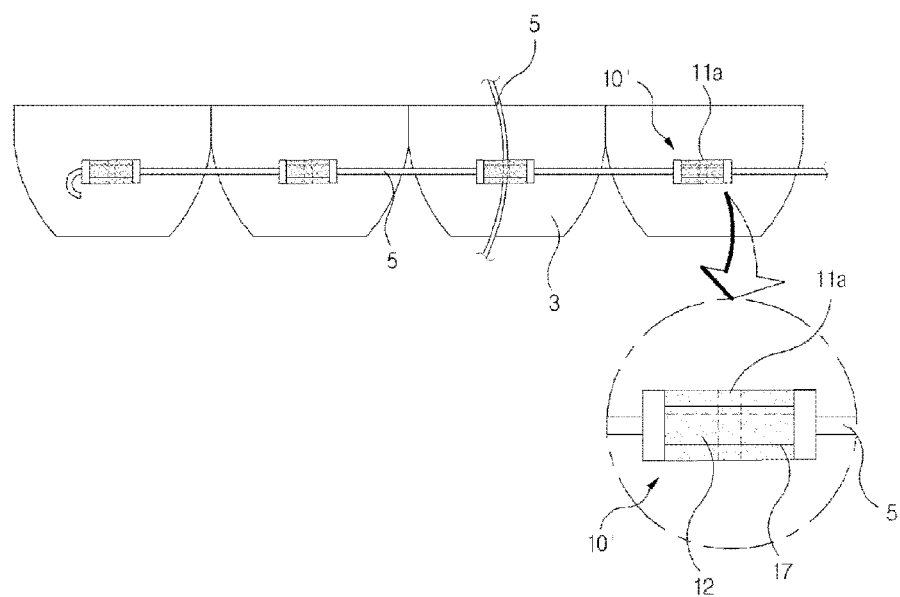
FIG. 11 is a view showing a state in which a wire is fastened to the orthodontic hole of FIG. 10A to correct a direction of a deviated tooth.

When the orthodontic hole 11a is formed as described above, after the tube 10' is completely adhered to the tooth 3 for orthodontic treatment, as shown in FIG. 11, the operator inserts the wire 5 into the tubes 10' adhered to the teeth 3 and then bends both ends of the inserted wire 5, performing the orthodontic treatment using the tube 10'.

Here, when the direction of the deviated tooth 3 such as an inturned tooth is to be corrected, the operator inserts the wire 5 into the orthodontic hole 11a formed in a direction perpendicular to the main-tube insertion tube 17 and then inserts the wire 5 into the orthodontic hole 11a of another adjacent tooth 3 to tighten the wire 5 such that a force of correcting the direction of the deviated tooth 3 can be received or to fix both ends thereof using a separate tightening mechanism or fastening mechanism, correcting the direction of the deviated tooth 3.

As can be seen from the foregoing, since the adhesive is applied to the adhesion space formed by fitting the pair of caps onto the outer circumference of the main tube, the caps can prevent the applied adhesive from flowing into the main tube and the wire can be easily inserted into the main tube.

In addition, since the operator can remove a portion of the cap according to necessity, the attachment height of the main tube attached to the tooth surface can be easily adjusted.

Further, since the adhesive can be evenly applied to the entire adhesion space, the main tube can be securely adhered to the tooth with sufficient adhesion strength and good appearance.

Furthermore, since the caps fitted onto both sides of the main tube can be easily gripped, the tube can be relatively easily separated from the tooth in comparison with the conventional tube.

In addition, since the tube guide projecting from both sides of the main tube by a predetermined length is inserted into the main tube, the operator can easily check the adhesion direction deviation state of the main tube during adhesion of the tube to the tooth surface for orthodontic treatment.

Further, when the dental cast tray is used to attach the tube in accordance with the present invention to the tooth surface through an indirect attachment method, even if the main tube is surface-treated through sandblasting in order to increase adhesion strength of the main tube disposed on the dental cast tray, the caps are fitted onto both sides of the main tube, or the tube guide is additionally inserted into the main tube. Accordingly, the tube cannot be easily separated from the dental cast tray.

Furthermore, since the adhesive is applied to the adhesion space formed on the outer circumference of the main-tube insertion tube by the pair of flanges, the flanges can prevent the applied adhesive from flowing into the main tube and the wire can be easily inserted into the main tube.

In addition, since the operator can remove a portion of the flanges according to necessity, the attachment height of the main-tube insertion tube attached to the tooth surface can be easily adjusted.

Further, since the adhesive can be evenly applied to the entire adhesion space, the main-tube insertion tube can be securely adhered to the tooth with sufficient adhesion strength and good appearance. In particular, since the main tube formed of a metal is inserted into the main-tube insertion tube to be covered therewith, the tube has a better appearance in comparison with the case in which the main tube is directly attached to the tooth.

Furthermore, since the flanges formed at both sides of the main-tube insertion tube can be easily gripped, the tube can be relatively easily separated from the tooth in comparison with the conventional tube.

In addition, since the tube guide projecting from both sides of the main-tube insertion tube by a predetermined length is inserted into the main tube, the operator can easily check the adhesion direction deviation state of the main-tube insertion tube during adhesion of the tube to the tooth surface for orthodontic treatment.

Further, when the dental cast tray is used to attach the tube in accordance with the present invention to the tooth surface through the indirect attachment method, even if the main-tube insertion tube is surface-treated through sandblasting in order to increase adhesion strength of the main-tube insertion tube disposed on the dental cast tray, the flanges are formed at both sides of the main-tube insertion tube, or the tube guide is additionally inserted into the main tube. Accordingly, the tube cannot be easily separated from the dental cast tray.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An orthodontic treatment tube comprising:
   a main tube having a hollow shape with a first insertion hole;
   a main-tube insertion tube having a second insertion hole into which the main tube is inserted, and a pair of flanges projecting from both ends of an outer circumference thereof to a predetermined width to form an adhesion space therebetween in which an adhesive is accommodated and the adhesive is prevented by the pair of flanges from flowing into the main tube through the insertion hole of the main tube, each of the pair of flanges having a groove with an acute angle inclined toward a corresponding end of the main-tube insertion tube; and
   a tube guide inserted into the first insertion hole of the main tube, the tube guide having both ends projecting from both sides of the main-tube insertion tube by a predetermined length so that an adhesion direction deviation state of the main-tube insertion tube can be easily checked during adhesion of the main-tube insertion tube to a tooth surface for orthodontic treatment, wherein a diameter of the second insertion hole of the main-tube insertion tube is the same as an outer diameter of the main tube.

2. The orthodontic treatment tube according to claim 1, wherein one or both of the pair of flanges are partially removed to adjust an attachment height of the main-tube insertion tube attached to a tooth surface.

3. The orthodontic treatment tube according to claim 1, wherein an orthodontic hole into which a wire can be fastened between a tooth surface and the adhesion space to correct a direction of a tooth is formed in a direction perpendicular to the main-tube insertion tube when the adhesive is applied to the adhesion space formed on the outer circumference of the main-tube insertion tube by the pair of flanges.

4. The orthodontic treatment tube according to claim 1, wherein a diameter of the tube guide is the same as a diameter of the first insertion hole of the main tube.

* * * * *